United States Patent [19]

Hansl

[11] 3,988,371

[45] Oct. 26, 1976

[54] META-[2-(BENZYLAMINO)-ETHYL] BENZOIC ACID AMIDES

[76] Inventor: Nikolaus R. Hansl, 7815 Pine St., Omaha, Nebr. 68124

[22] Filed: July 30, 1974

[21] Appl. No.: 493,160

Related U.S. Application Data

[63] Continuation-in-part of Ser. No. 233,339, March 9, 1972, abandoned, which is a continuation-in-part of Ser. No. 85,283, Oct. 29, 1970, Pat. No. 3,792,048, and a continuation-in-part of Ser. No. 745,352, July 17, 1968, abandoned.

[52] U.S. Cl............... 260/558 A; 260/247.2 A; 260/247.5 R; 260/247.5 F; 260/247.5 C; 260/247.5 H; 260/268 R; 260/268 C; 260/268 H; 260/293.64; 260/293.77; 260/326.25; 260/326.41; 260/326.5 E; 260/559 A; 260/293.71; 424/248; 424/250; 424/267; 424/274; 424/324

[51] Int. Cl.$^2$.................................... C07C 103/28

[58] Field of Search.................. 260/558 A, 559 A

[56] References Cited

OTHER PUBLICATIONS

Chemical Abstracts 31: 5794–5795 (1937) Wegler et al.

*Primary Examiner*—Sherman D. Winters
*Attorney, Agent, or Firm*—Murray and Whisenhunt

[57] ABSTRACT

A series of substituted amino ethyl meta benzoic acid amides and their salts are useful as spasmolytics, pschyotherapeutic agents and agents facilitating learning. These compounds may conveniently be prepared by hydrolysis of suitably substituted trifluoromethyl derivatives followed by amidification with a desired amine, or by a replacement reaction between a suitable ester and an appropriate amine, or by reaction of an activated form of the free acid and an appropriate amine.

1 Claim, No Drawings

META-[2-(BENZYLAMINO)-ETHYL] BENZOIC ACID AMIDES

RELATED APPLICATIONS

This application is a continuation-in-part of copending U.S. Pat. application Ser. No. 233,339, filed Mar. 9, 1972, which is a continuation-in-part of copending U.S. Pat. application Ser. No. 745,352, filed July 17, 1968, titled "AMINOALKYLBENZOIC ACID DERIVATIVES," both now abandoned, and Ser. No. 85,283, filed Oct. 29, 1970, titled "AMINO-ALKYL-BENZOIC ACID DERIVATIVES," now U.S. Pat. No. 3,792,048.

BACKGROUND OF THE INVENTION m-aminoethyl benzoic acid is described in Chemical Abstracts 52, 6404. Ortho-N-methylaminoethyl benzoic acid and its diethyl amide is disclosed in Chemical Abstracts 31, 5795. The diethylamide of o-diethylaminoethyl benzoic acid is disclosed in Chemical Abstracts 31, 5795. Various p-(amino-alkyl benzoic acids and amides are disclosed in Chemical Abstracts 38, 732.

BRIEF DESCRIPTION OF THE INVENTION

The present invention relates to a series of substituted aminoethyl meta benzoic acid amides and their salts which compounds are useful as spasmolytics, psychotherapeutic agents and agents facilitating learning. The compounds of the present invention have the general structural formula

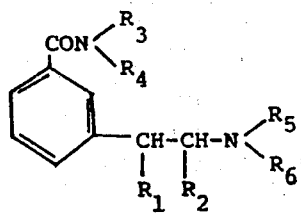

I wherein $R_1$ is hydrogen, hydroxy, lower alkoxy or lower alkyl; $R_2$ is hydrogen or lower alkyl; $R_3$ taken independently is hydrogen, lower alkyl, aralkyl, lower alkyl aryl; $R_4$ taken independently is hydrogen, lower alkyl, aralkyl, lower alkyl aryl; and $R_3$ and $R_4$ taken together with the adjacent nitrogen atom form a saturated five or six membered heterocyclic ring which may contain one additional hetero atom selected from the group consisting of —O— and $NR_7$— where $R_7$ is hydrogen or lower alkyl; $R_5$ taken independently is lower alkyl, aralkyl, lower alkyl aryl or lower alkoxy aralkyl; $R_6$ taken independently is hydrogen, lower alkyl, aralkyl, or lower alkyl aryl and $R_5$ and $R_6$ taken together with the adjacent nitrogen atom form a saturated five or six membered heterocyclic ring which may contain one additional hetero atom selected from the group consisting of —O— and $NR_7$— where $R_7$ is hydrogen or lower alkyl; and the pharmaceutically acceptable acid addition salts thereof.

As used herein the term "lower" includes radical groups containing from 1 to 7 carbon atoms. The term "alkyl" is meant to include straight or branched chain hydrocarbon radicals such as methyl, ethyl, n-propyl, t-butyl, hexyl, heptyl, and the like. The term "alkoxy" is meant to include a radical group wherein an alkyl moiety is bonded to an oxygen atom through an ether linkage, the valence or the radical being derived from said oxygen atom. Suitable examples of alkoxy groups include methoxy, ethoxy, butoxy and the like. The term "aralkyl" is meant to include radical groups such as phenyl lower alkyl, especially radical groups such as benzyl, phenylethyl and the like. "Lower alkyl aryl" is meant to encompass groups such as lower alkyl phenyl, particularly tolyl xylyl and the like. The term "lower alkoxy lower alkyl" is meant to include radical groups such as methoxy methyl, methoxy ethyl, ethoxy methyl, ethoxy ethyl, and the like. Examples of suitable heterocyclic radical groups obtained when $R_5$ and $R_6$ are taken together with the adjacent nitrogen atom include morpholino, piperidino, piperazino and N-lower alkyl piperazino.

The compounds of formula I form acid addition salts with a variety of inorganic and organic acids. Suitable inorganic acids for this purpose include the hydrohalic acids such as hydrochloric and hydrobromic acids, sulfuric acid, phosphoric acid, sulfamic acid and the like. Suitable organic acids for this purpose include tartaric acid, citric acid, maleic acid, hexonic acid, and the like. Comounds of formula I in the form of acid addition salts with pharmaceutically unacceptable acids can be converted to acid addition salts with pharmaceutically acceptable acids by ion exchange procedures known in the art.

Preferred compounds of formula I of the present invention are obtained when $R_1$ is hydrogen or lower alkoxy, preferably methoxy, $R_2$ is hydrogen, $R_3$ is lower alkyl, $R_4$ is hydrogen or lower alkyl and $R_5$ is lower alkyl, aralkyl, preferably benzyl or parachloro benzyl. Exemplary of compounds of the present invention are the following:

m-[2-(benzylamino)-ethyl] benzamide
m-[2-(benzylamino)-ethyl] benzoic acid methyl amide
m-[2-(benzylamino)-ethyl] benzoic acid benzyl amide
m-[2-(cyclohexylamino)-ethyl] benzoic acid pyrrolidine amide
m-[2-(benzylamino)-ethyl] benzoic acid diethyl amide Compounds of formula I are conveniently prepared by hydrolysis if suitably substituted trifluoromethyl derivatives of the formula

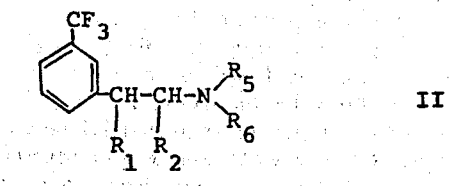

II where $R_1$, $R_2$, $R_5$ and $R_6$ are as above followed by amidification with a desired amine of the formula $HNR_3R_4$ where $R_3$ and $R_4$ are as above.

The hydrolysis is conducted in the presence of a strong acid, preferably concentrated sulfuric acid. The amine is added in the form of its salt with an acid which in its anhydrous form is a gas such as hydrochloric acid. In lieu of excess salt of the reactive amine a salt such as the hydrochloride salt of a nonreactive tertiary amine such as triethylamine hydrochloride may be used to neutralize excess sulfuric acid. When the HCl evolution has nearly ceased, a small excess of reactive amine is added. The reaction mixture is heated to between 40° and 120° C for approximately one hour. The cooled reaction mixture is poured into ice water and the amide purified following conventional extraction and recrystallization procedures.

It is also within the scope of the present invention to employ alternate procedures for the preparation of the amides of formula I from the esters of formula

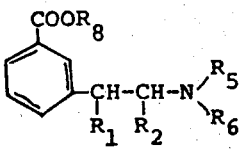           III where $R_1$, $R_2$, $R_5$ and $R_6$ are as above and where $R_8$ is lower alkyl by reacting with amines of the formula

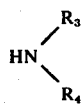

wherein $R_3$ and $R_4$ are as above.

It is also within the scope of the present invention to employ other alternate procedures for the preparation of the amides of formula I from the acids of formula IV

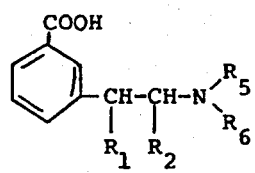           IV where $R_1$, $R_2$, $R_5$ and $R_6$ are as above. For example, activated derivatives of the carboxyl moiety such as an acid halide; i.e., acid chloride can be utilized in the amidification reaction. These activated derivatives can be prepared from the benzoic acids of formula IV by procedures well known in the art.

It is also within the scope of the present invention to prepare compounds of formula I bearing additional non-interfering groups on the aromatic ring. Such non-interfering groups include lower alkyl, halogen, hydroxy, lower alkoxy, nitro, sulfato and the like. Furthermore, compounds of formula I may contain asymmetric carbon atoms in the ethylene sidechain depending on secondary substitution or asymmetric centers in other places. Racemic mixtures as well as the optical enantiomers of such compounds are to be considered within the scope of this invention. Racemate pairs can be separated by conventional resolution procedures, such as, for example, fractional crystallization of diastereomer salts formed with an optically active acid; i.e., tartaric acid, camphorsulfonic acid and the like. Chromatographic procedures for effecting such resolution are also known in the art.

The compounds of formula I of the present invention are useful in facilitating certain parameters of intellectual performance in the experimental animal; such as, for example, the enhancement of learning and memory. Additionally, the compounds of formula I are useful as spasmolytic agents. These compounds can be administered for prolonged periods of time.

The spasmolytic activity of the instant compounds can be demonstrated by the effect on the isolated rabbit ileum stimulated by such spasmogens as acetyl choline, barium chloride and histamine. The psychotropic activity can be demonstrated through the effect of instant compounds on the motor activity of rodents.

Using m-[2-(benzylamino)-ethyl] benzamide as the test compound, it was found that a compound of this structure reduces motor activity in the rodent in a dose of 2 mg/kg by as much as 53 per cent of control values. The effect on learning was demonstrated in active avoidance paradigms using electric shock as stimulus. Using rats as experimental animals the compound m-[2-(benzylamino)-ethyl] benzoic acid methyl amide was found to improve performance at the 1 mg/kg level.

When utilized to enhance mental performance in higher mammals, the compounds of formula I, may be administered in oral dosages in the same range of from about 0.01 to about 4 mg/kg, preferably in the range of from about 0.01 to about 2 mg/kg, most preferably from about 0.05 to about 1.2 mg/kg. Parenteral dosages of about 10 to 100 times these levels are preferred in laboratory test animals.

The desired compounds of this invention are employed in the described uses in the form of nontoxic acid addition salts and may be administered to mammalians as pure compounds. It is advisable, however, to first combine one or more of the novel compounds with a suitable pharmaceutical carrier to attain a more satisfactory size to dosage relationship.

Pharmaceutical carriers which are liquid or solid may be used, the preferred liquid carrier being water in a pharmaceutically acceptable emulsion, suspension or solution. Flavoring materials may be included in the solutions as desired.

Solid pharmaceutical carriers such as starch, sugar, talc, mannitol and the like may be used to form powders. The powders may be given directly or incorporated in tablet, capsule or suppository preparations.

EXAMPLE I

A total of 2.5g of m-[2-(benzylaminoethyl)-benzoic acid] methyl ester hydrochloride was dissolved in a mixture of 30g dioxane and 10g water and 10g anhydrous ammonia. The resultant solution was kept at room temperature in a pressure bottle for a prolonged period of time. Removal of excess ammonia and excess solvent in vacuo, addition of HCl, and recrystallization from acetone yielded 1.69g (72 per cent) of material consisting of m-[2-(benzylamino)-ethyl] benzamide hydrochloride melting at 273° – 275° C.

Analysis: Calculated for $C_{16}H_{18}N_2O$ . HCl : N., 9.63 per cent. Found : N., 9.39 per cent.

EXAMPLE II

A total of 2.5g of m-[2-(benzylamino)-ethyl] benzoic acid methyl ester was dissolved in a mixture of 50g of dioxane and 30g of 40 per cent aqueous monomethylamine. The resultant solution was kept at room temperature in a pressure bottle for a prolonged period of time. Removal of excess monomethylamine and solvent in vacuo left an oily residue which solidified on standing. After conversion to the hydrochloride salt and recrystallization from isopropanol — ether 1.36g (54.5 per cent) of material consisting of m-[2-(benzylamino)-ethyl] benzoic acid methyl amide hydrochloride was obtained melting at 248° – 249° C.

Analysis: Calculated for $C_{16}H_{18}N_2O$ . HCl Cl⁻ 11.66 per cent.

Found: Cl 11.7 per cent.

EXAMPLE III

A total of 1.34g of m-[2-(benzylamino)-ethyl] benzoic acid methyl ester hydrochloride was mixed with 5g benzylamine and 0.03g methanol. The reaction mixture was heated to 135° C to 155° C for 11 hours. The resultant solution was cooled and the excess benzylamine removed in vacuo. The semisolid residue was converted to the hydrochloride and recrystallized from methanolisopropanol-ether. 600 mg (32.5 per cent) of material consisting of m-[2-(benzylamino)-ethyl]-benzoic acid benzyl amide hydrochloride melting at 242°–244° C was obtained.

Analysis: Calculated for $C_{23}H_{24}N_2O$ .HCl Cl⁻ 9.32 per cent.

Found: Cl⁻ 9.28 per cent.

EXAMPLE IV

A total of 1.5g of m-[2-(cyclohexylamino)-ethyl] benzoic acid ethyl ester hydrochloride was added to 5g pyrrolidine and 0.03g ethylene glycol. The reaction mixture was heated to 130° for 48 hours. Excess pyrrolidine was removed in vacuo. The residue was taken up in isopropanol and ether HCl was added. The product crystallized on standing and was recrystallized from isopropanol-ether. The material consisting of m-[2-(cyclohexylamino)-ethyl] benzamido pyrrolidine was obtained in 46 per cent yield (740 mg) and melted at 170°–172° C.

Analysis: Calculated for $C_{19}H_{28}N_2O$ .HCl Cl⁻ 9.5 per cent.

Found Cl⁻ 9.43 per cent.

EXAMPLE V

A total of 5 g of N-benzyl-3-trifluoromethyl-phenethylamine hydrochloride was dissolved in 20 g concentrated sulfuric acid and the resultant solution was heated on an oil bath for 1 hour (Temp. 95° C). To the cooled reaction mixture was added 10.9 g of diethylamine hydrochloride and the resultant mixture heated for 1 hour at 95° C. The reaction mixture was now cooled to room temperature and poured into ice water. The solution was made alkaline with ammonia and concentrated. A solid base was isolated. Conversion of this solid to the hydrochloride and recrystallization from methanol-isopropanol-ether yielded 3.1 g (56 per cent) of m-[2-(benzylamino ethyl) benzoic acid] diethyl amide melting at 271°–272° C.

Analysis: Calculated for $C_{20}H_{26}N_2O$ .HCl N., 8.08 per cent.

Found: N., 8.32 per cent.

EXAMPLE VI

A total of 1.37 g of N-Benzyl-3-trifluoromethylphenethylamine hydrochloride was mixed with 5 g of Cyclohexylamine and 0.06 g of methonal. The mixture was heated for 7 hours at 140° C. Excess cyclohexylamine was removed in vacuo. The residue dissolved in iso-propanol and converted to the hydro-chloride salt. After recrystallization, 150 mg of m-[2-(benzylamino) ethyl] benzoic acid cyclohexamide hydrochloride melting at 248°–249° C was obtained.

Analysis: Calculated for $C_{22}H_{28}N_2O$ .HCl; Cl⁻ 10.48 per cent.

Found: Cl⁻ 10.56 per cent.

I claim:

1. A compound selected from the group consisting of m-[2-(benzylamino)-ethyl] benzamide, m-[2-(benzylamino)-ethyl] benzoic acid methyl amide, m-[2-(benzylamino)-ethyl] benzoic acid benzyl amide, m-[2-(benzylamino)-ethyl] benzoic acid diethyl amide, and m-[2-(benzylamino)-ethyl] benzoic acid cyclohexamide, or the optical antipode or the pharmaceutically-acceptable acid addition salt thereof.

* * * * *